(12) United States Patent
Poppi et al.

(10) Patent No.: US 11,390,409 B2
(45) Date of Patent: Jul. 19, 2022

(54) STERILIZATION APPARATUS, PACKAGING MACHINE HAVING A STERILIZATION APPARATUS AND A METHOD FOR STERILIZING

(71) Applicant: TETRA LAVAL HOLDINGS & FINANCE S.A., Pully (CH)

(72) Inventors: Luca Poppi, Formigine (IT); Filippo Ferrarini, Modena (IT)

(73) Assignee: TETRA LAVAL HOLDINGS & FINANCE S.A., Pully (CH)

( * ) Notice: Subject to any disclaimer, the term of this patent is extended or adjusted under 35 U.S.C. 154(b) by 0 days.

(21) Appl. No.: 17/045,011

(22) PCT Filed: Mar. 26, 2019

(86) PCT No.: PCT/EP2019/057606
§ 371 (c)(1),
(2) Date: Oct. 2, 2020

(87) PCT Pub. No.: WO2019/192899
PCT Pub. Date: Oct. 10, 2019

(65) Prior Publication Data
US 2021/0139180 A1 May 13, 2021

(30) Foreign Application Priority Data
Apr. 3, 2018 (EP) .................................. 18165369

(51) Int. Cl.
*B65B 55/08* (2006.01)
*B65B 55/10* (2006.01)
*A61L 2/08* (2006.01)

(52) U.S. Cl.
CPC ............ *B65B 55/08* (2013.01); *B65B 55/103* (2013.01); *A61L 2/087* (2013.01); *A61L 2202/122* (2013.01); *A61L 2202/14* (2013.01)

(58) Field of Classification Search
CPC ......... B65B 55/08; B65B 55/103; B65B 9/06; A61L 2/087; A61L 2202/122; A61L 2202/14; A61L 2/08
See application file for complete search history.

(56) References Cited

U.S. PATENT DOCUMENTS

| 8,658,085 B2 | 2/2014 | Kristiansson et al. |
| 2005/0126117 A1 | 6/2005 | Benedetti et al. |

(Continued)

FOREIGN PATENT DOCUMENTS

| CN | 1809496 A | 7/2006 |
| CN | 101588969 A | 11/2009 |

(Continued)

OTHER PUBLICATIONS

U.S. Appl. No. 17/044,655, filed Oct. 1, 2020, Filippo Ferrarini et al.

(Continued)

*Primary Examiner* — Sean E Conley
*Assistant Examiner* — Brendan A Hensel
(74) *Attorney, Agent, or Firm* — Buchanan Ingersoll & Rooney PC

(57) ABSTRACT

A sterilization apparatus for sterilizing a web of packaging material advancing along a web advancement path-comprises an irradiation device for sterilizing the advancing packaging material web, a main shielding chamber housing the irradiation device and comprising an advancement channel having an inlet opening and an outlet opening and through which, in use, the packaging material web advances along the sterilization portion, an auxiliary shielding chamber upstream of the advancement channel along the web advancement path, the auxiliary shielding chamber having an inner space in fluid connection with the advancement channel and comprising an extraction opening allowing gas (Continued)

extraction from the auxiliary shielding chamber. An aspiration device generates a first flow of gas within the advancement channel from the outlet opening to the inlet opening and a second flow of gas from the inlet opening to the extraction opening.

12 Claims, 4 Drawing Sheets

(56) References Cited

U.S. PATENT DOCUMENTS

2006/0284111 A1    12/2006   Naslund et al.
2010/0005760 A1    1/2010   Matheyka

FOREIGN PATENT DOCUMENTS

| EP | 3 009 362 A1 | 4/2016 | |
| WO | 2004110868 A1 | 12/2004 | |
| WO | WO-2004110868 A1 * | 12/2004 | ............. A61L 2/087 |

OTHER PUBLICATIONS

Office Action (First Office Action) dated Mar. 26, 2021, by the State Intellectual Property Office of People's Republic of China in corresponding Chinese Patent Application No. 201980024525.X and an English Translation of the Office Action. (26 pages).

International Search Report (PCT/ISA/210) dated May 7, 2019, by the European Patent Office as the International Searching Authority for International Application No. PCT/EP2019/057606.

Written Opinion (PCT/ISA/237) dated May 7, 2019, by the European Patent Office as the International Searching Authority for International Application No. PCT/EP2019/057606.

* cited by examiner

STERILIZATION APPARATUS, PACKAGING MACHINE HAVING A STERILIZATION APPARATUS AND A METHOD FOR STERILIZING

TECHNICAL FIELD

The present invention relates to a sterilization apparatus for sterilizing a web of packaging material, in particular a web of packaging material for the production of sealed packages of a pourable product, in particular a pourable food product.

The present invention also relates to a packaging machine for producing sealed packages of a pourable product, in particular a pourable food product, having a sterilization apparatus.

The present invention also relates to a method for sterilizing a web of packaging material, in particular a web of packaging material for the production of sealed packages of a pourable product, in particular a pourable food product.

BACKGROUND ART

As is known, many liquid or pourable food products, such as fruit juice, UHT (ultra-high-temperature treated) milk, wine, tomato sauce, etc., are sold in packages made of sterilized packaging material.

A typical example is the parallelepiped-shaped package for liquid or pourable food products known as Tetra Brik Aseptic (registered trademark), which is made by sealing and folding laminated strip packaging material. The packaging material has a multilayer structure comprising a base layer, e.g. of paper, covered on both sides with layers of heat-seal plastic material, e.g. polyethylene. In the case of aseptic packages for long-storage products, such as UHT milk, the packaging material also comprises a layer of oxygen-barrier material (an oxygen-barrier layer), e.g. an aluminum foil, which is superimposed on a layer of heat-seal plastic material, and is in turn covered with another layer of heat-seal plastic material forming the inner face of the package eventually contacting the food product.

Packages of this sort are normally produced on fully automatic packaging machines, which advance a web of packaging material from a magazine unit through a sterilization apparatus for sterilizing the web of packaging material and to an isolation chamber (a closed and sterile environment) in which the sterilized web of packaging material is maintained and advanced. During advancement of the web of packaging material through the isolation chamber, the web of packaging material is folded and sealed longitudinally to form a tube having a longitudinal seam portion, which is further fed along a vertical advancing direction.

In order to complete the forming operations, the tube is filled with a sterilized or sterile-processed pourable product, in particular a pourable food product, and is transversally sealed and subsequently cut along equally spaced transversal cross sections within a package forming unit of the packaging machine during advancement along the vertical advancing direction.

Pillow packages are so obtained within the packaging machine, each pillow package having a longitudinal sealing band, a top transversal sealing band and a bottom transversal sealing band.

In the recent years, sterilization apparatuses have become available, which are configured to sterilize the web of packaging material by means of the application of physical irradiation, in particular electromagnetic irradiation, even more particular electron beam irradiation.

A typical sterilization apparatus of this kind comprises an irradiation device typically having a pair of electron beam emitters spaced apart from one another. An advancement channel, through which, in use, the web of packaging material advances, is interposed between the electron beam emitters. Each one of the electron beam emitters is adapted to direct the respective electron beam onto one respective face of the web of packaging material advancing through the advancement channel.

Furthermore, such a kind of sterilization apparatus must provide for means that guarantee to safely discharge ozone and other undesired components, which may form during the application of the sterilizing irradiation.

For this reason, a typical sterilization apparatus sterilizing by means of a sterilizing irradiation comprises a main shielding chamber housing the irradiation device, a first auxiliary shielding chamber connected to the main shielding chamber and arranged upstream of the main shielding chamber and a second auxiliary shielding chamber connected to the main shielding chamber and being arranged downstream of the main shielding chamber. In use, the un-sterilized web of packaging material enters the first auxiliary shielding chamber, is sterilized within the main shielding chamber and the sterilized web of packaging material enters the second auxiliary shielding chamber from where it advances into the isolation chamber.

Furthermore, the sterilization apparatus also comprises an isolation housing, which houses in its inner space the main shielding chamber, the first auxiliary shielding chamber and the second auxiliary shielding chamber and from which any undesired components are extracted.

Thus, such a sterilization apparatus comes along with a rather complex design, in particular requiring the presence of the isolation housing.

Even though this kind of sterilization apparatus and, accordingly, also the packaging machine provides for good results, a desire is felt to simplify the design of these kinds of sterilization apparatus sterilizing by means of the application of sterilizing irradiation.

DISCLOSURE OF INVENTION

It is therefore an object of the present invention to provide a sterilization apparatus to overcome, in a straightforward and low-cost manner, at least one of the aforementioned drawbacks.

In particular, it is an object of the present invention to provide a sterilization apparatus, which comes along with a simplified design.

It is a further object of the present invention to provide a packaging machine to overcome, in a straightforward and low-cost manner, at least one of the aforementioned drawbacks.

In particular, it is an object of the present invention to provide a packaging machine, which comes along with a simplified design.

It is a further object of the present invention to provide a method for sterilizing to overcome, in a straightforward and low-cost manner, at least one of the aforementioned drawbacks.

According to the present invention, there is provided a sterilization apparatus as claimed in claim 1.

According to the present invention, there is also provided a packaging machine according to claim 8.

According to the present invention, there is also provided a method for sterilizing according to claim 10.

Preferred embodiments are claimed in the dependent claims.

BRIEF DESCRIPTION OF THE DRAWINGS

A non-limiting embodiment of the present invention will be described by way of example with reference to the accompanying drawings, in which.

BEST MODES FOR CARRYING OUT THE INVENTION

Figure 1:
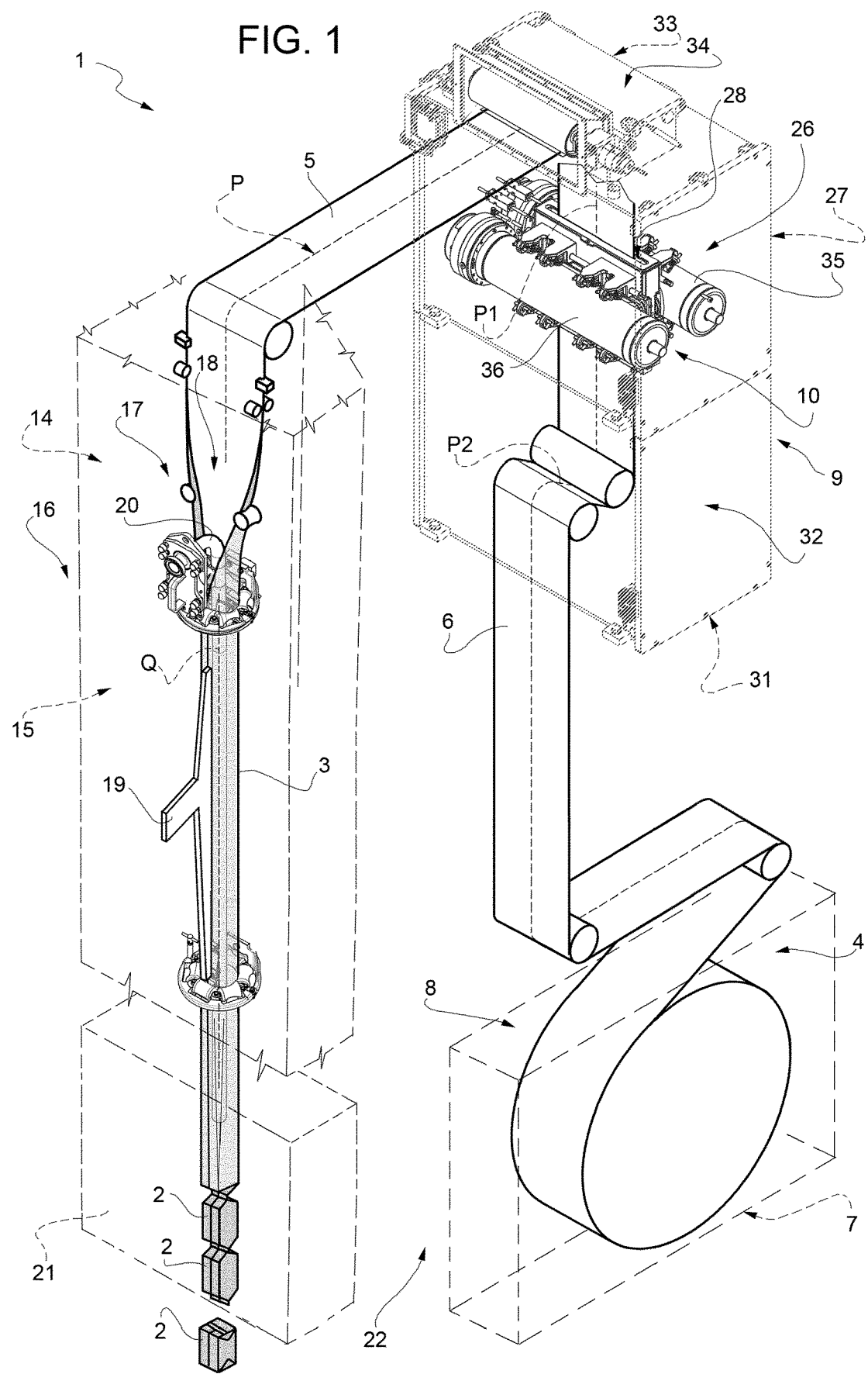
FIG. 1 is a schematic view of a packaging machine having a sterilization apparatus according to the present invention, with parts removed for clarity.

Number 1 indicates as a whole a packaging machine for producing sealed packages 2 of a pourable product, in particular a pourable food product such as pasteurized milk, fruit juice, wine, tomato sauce, etc., from a tube 3 of a web 4 of packaging material. In particular, in use, tube 3 extends along a longitudinal axis, in particular having a vertical orientation.

Web 4 at least comprises a layer of fibrous material, in particular paper, covered on both sides with respective layers of heat-seal plastic material, e.g. polyethylene.

Preferably, web 4 also comprises a layer of gas- and light-barrier material, e.g. aluminum foil or ethylene vinyl alcohol (EVOH) film, and at least a first layer and a second layer of heat-seal plastic material. The layer of gas- and light-barrier material is superimposed on the first layer of heat-seal plastic material, and is in turn covered with the second layer of heat-seal plastic material. The second layer of heat-seal plastic material forms the inner face of package 2 eventually contacting the filled pourable food product.

More specifically, web 4 comprises a first face 5 and a second face 6, in particular first face 5 being the face of web 4 forming the inner face of the formed package 2 eventually contacting the filled pourable food product.

A typical package 2 obtained by packaging machine 1 comprises a longitudinal seam portion and a pair of transversal sealing bands, in particular a transversal top sealing band and a transversal bottom sealing band.

With particular reference to FIG. 1, packaging machine 1 is configured to advance web 4 along a web advancement path P, to sterilize web 4 during advancement along path P, to form tube 3 from web 4 and to fill tube 3 and to form single packages 2 from the filled tube 3.

Preferentially, packaging machine 1 comprises:
a magazine unit 7 adapted to provide for web 4 at a host station 8;
a sterilization apparatus 9 configured to sterilize at least first face 5, preferentially also second face 6, of web 4 at a sterilization station 10, arranged downstream of host station 8 along path P;
an isolation chamber 14 connected to sterilization apparatus 9 and separating an inner environment 15, in particular an inner sterile environment, from an outer environment 16 and being configured to receive the sterilized web 4 from sterilization apparatus 9;
a tube forming device 17 extending along a longitudinal axis, in particular having a vertical orientation, and being arranged, in particular at a tube forming station 18, at least partially, preferably fully, within isolation chamber 14 and being adapted to form tube 3 from the, in use, advancing and sterilized web 4;
a sealing device 19 at least partially arranged within isolation chamber 14 and being adapted to longitudinally seal tube 3 formed by tube forming device 17 so as to form a longitudinal seam portion of tube 3;
filling means 20 for filling tube 3 with the pourable product, in particular the pourable food product;
a package forming unit 21 adapted to at least form and transversally seal tube 3, in particular the, in use, advancing tube 3, for forming packages 2; and
conveying means 22 for advancing in a known manner web 4 along path P from host station 8 to tube forming station 18 and to advance tube 3 along a tube advancement path Q towards and at least partially through package forming unit 21.

Preferentially, packaging machine 1 also comprises pressure control means configured to control the pressure within at least isolation chamber 14 and within at least portions of sterilization apparatus 9.

In particular, sterilization station 10 is arranged upstream of tube forming station 17. In other words, sterilization apparatus 9 is arranged upstream of isolation chamber 14 along path P.

Preferentially, sterilization apparatus 9 is arranged downstream of magazine unit 7 along path P.

In particular, package forming unit 21 is arranged downstream of isolation chamber 14 and tube forming device 17 along path Q.

Preferentially, conveying means 22 are adapted to advance tube 3 and any intermediate of tube 3 in a manner known as such along path Q, in particular from tube forming station 18 towards and at least partially through package forming unit 21. In particular, with intermediates of tube 3 any configuration of web 4 is meant prior to obtaining the tube structure and after folding of web 4 by tube forming device 16 has started. In other words, the intermediates of tube 3 are a result of the gradual folding of web 4 so as to obtain tube 3, in particular by overlapping opposite lateral edges of web 4 with one another.

With particular reference to FIG. 1, sterilization apparatus 9 comprises:
an irradiation device 26 arranged in the area of sterilization station 10 and being adapted to sterilize at least first face 5, preferentially also second face 6, by directing a sterilizing irradiation, in particular electromagnetic irradiation, even more particular electron beam irradiation, onto at least first face 5, preferentially also onto second face 6, while, in use, web 4 advances along a sterilization portion P1 of path P;
a main shielding chamber 27 housing the irradiation device and comprising an advancement channel 28, in particular extending along a longitudinal axis, having an inlet opening 29 and an outlet opening 30 arranged downstream of inlet opening 29 along path P, and through which, in use, web 4 advances along sterilization portion P1;
a first auxiliary shielding chamber 31 being arranged upstream of advancement channel 28 along path P and having a respective first inner space 32 being in fluid connection with advancement channel 28.

Preferentially, sterilization apparatus 9 also comprises a second auxiliary shielding chamber 33 being arranged downstream of advancement channel 28 along path P and having a second inner space 34 being fluidically connected to advancement channel 28 and inner environment 15.

In particular, advancement channel 28 is interposed between the first inner space 32 and the second inner space 34.

Preferentially, each one of inlet opening 29 and outlet opening 30 extends along a respective extension axis, the respective extension axes being parallel to one another.

It should be noted that main shielding chamber 27, in particular also first auxiliary shielding chamber 31, even more particular also second auxiliary shielding chamber 33 are configured to shield the sterilizing irradiation, in particular the electromagnetic irradiation, even more particular the electron beam irradiation. The shielding allows to avoid that any sterilizing irradiation, in particular electromagnetic irradiation, even more particular electron beam irradiation, penetrates out of sterilization apparatus 9.

Figure 2:
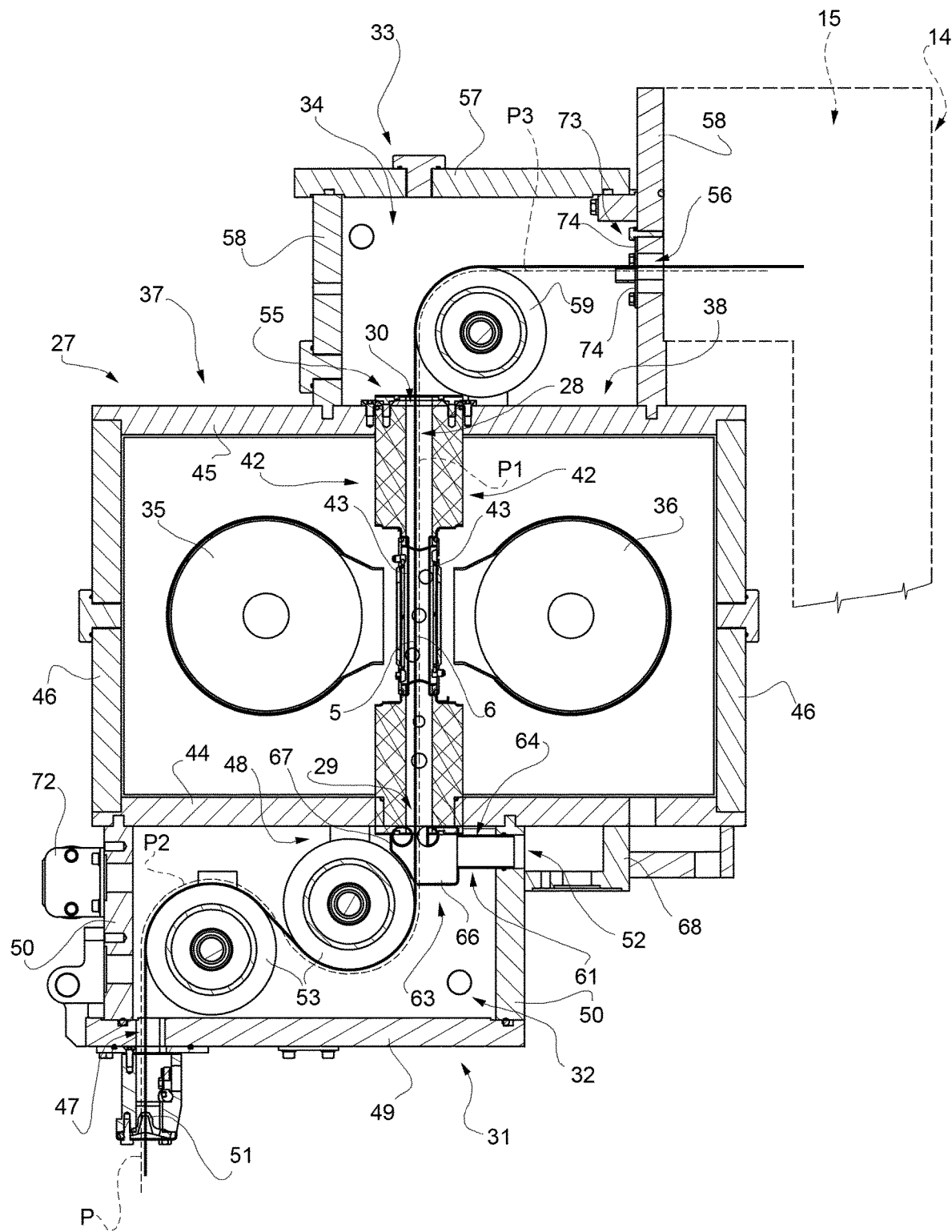
FIG. 2 is a sectionized view of the sterilization apparatus of FIG. 1, with parts removed for clarity.

With particular reference to FIGS. 1 and 2, irradiation device 26 comprises:
- at least a first irradiation emitter, in particular a first electron beam emitter 35, configured to direct the sterilizing irradiation, in particular the electromagnetic irradiation, even more particular the electron beam irradiation, in use, on first face 5; and
- preferentially also a second irradiation emitter, in particular a second electron beam emitter 36, configured to direct the sterilizing irradiation, in particular the electromagnetic irradiation, even more particular the electron beam irradiation, in use, on second face 6.

Preferably, first electron beam emitter 35 and second electron beam emitter 36 are arranged side-by-side and distanced from one another so that at least a portion of advancement channel 28 is interposed between first electron beam emitter 35 and second electron beam emitter 36.

In particular, first electron beam emitter 35 is placed such to face, in use, first face 5 and second electron beam emitter 36 is placed such to face, in use, second face 6.

In even further detail, first electron beam emitter 35 is arranged within a first portion 37 of main shielding chamber 27 and second electron beam emitter 36 is arranged within a second portion 38 of main shielding chamber 27. Preferentially, the advancement channel 28 is interposed between the first portion 37 and the second portion 38.

With particular reference to FIG. 2, main shielding chamber 27 comprises two inner walls 42 at least partially delimiting advancement channel 28. In particular, inner walls 42 are parallel to one another and distanced from one another so that the space between inner walls 42 defines advancement channel 28.

Preferentially, one inner wall 42 delimits first portion 37 and the other inner wall 42 delimits second portion 38.

More specifically, each inner wall 42 comprises a respective exit window 43 configured to allow the transmission of electron beam irradiation. In particular, in use, first electron beam emitter 35 and second electron beam emitter 36 transmit the electron beam irradiation onto respective first face 5 and second face 6 through the respective exit window 43.

In further detail, main shielding chamber 27 comprises a first principal wall 44 comprising inlet opening 29 and a second principal wall 45 comprising outlet opening 30, first principal wall 44 and second principal wall 45 being parallel to and distanced from one another. Main shielding chamber 27 is arranged such that, in use, second principal wall 45 is arranged downstream of second principal wall 44 along path P.

Preferentially, inner walls 42 are transversally, in particular perpendicularly, mounted to and are interposed between first principal wall 44 and second principal wall 45.

Preferably, main shielding chamber 27 also comprises outer lateral walls 46 being parallel to inner walls 42 and being interposed between and connected to first principal wall 44 and second principal wall 45.

Figure 3:
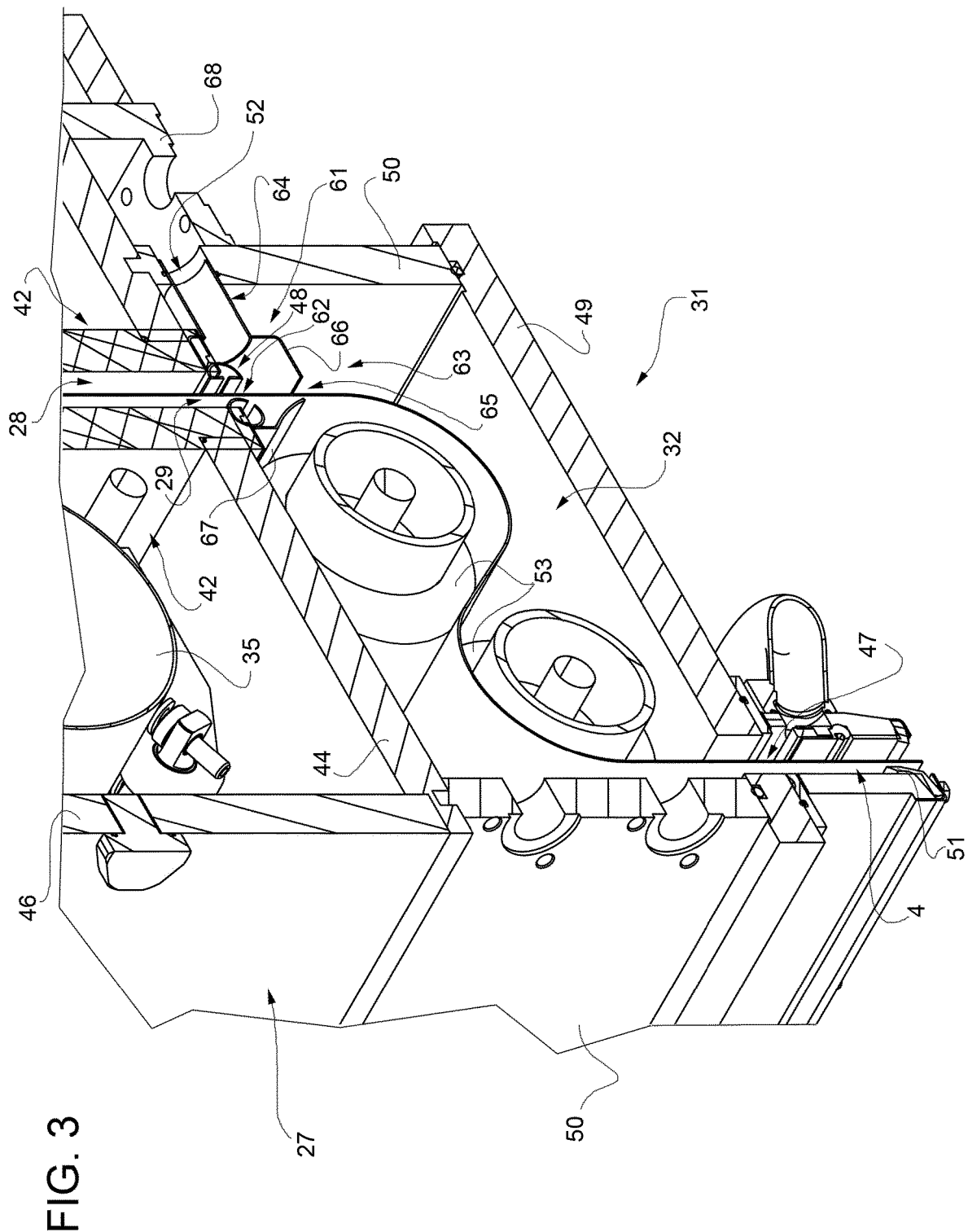
FIG. 3 is a partially sectionized and perspective view of a detail of the sterilization apparatus of FIG. 2.

With particular reference to FIGS. 2 and 3, first auxiliary shielding chamber 31 comprises an access opening 47 and a discharge opening 48 for web 4, in particular through which, in use, web 4 respectively enters into and exits from first auxiliary shielding chamber 31.

Preferentially, access opening 47 and inlet opening 29 are non-coaxially arranged with respect to one another. In other words, access opening 47 is arranged with respect to inlet opening 29 such that an imaginary line extending from access opening 47 to inlet opening 29 is inclined with respect to an imaginary line extending from inlet opening 29 to outlet opening 30 of advancement channel 28. In even other words, a projection of inlet opening 29 and a projection of access opening 47 onto a projection surface are transversally displaced from one another. In this way, a shielding effect of the sterilizing irradiation is guaranteed in the prolongation of advancement channel 28.

Preferentially, first auxiliary shielding chamber 31 is connected to, in particular mounted to, main shielding chamber 27. In particular, first auxiliary shielding chamber 31 is positioned such that, in use, first auxiliary shielding chamber 31 is arranged upstream of main shielding chamber 27 along path P.

In more detail, first auxiliary shielding chamber 31 comprises a principal plate 49, in particular parallel to first principal wall 44 and second principal wall 45, and outer lateral plates 50 connected to, in particular mounted to, principal plate 49 and laterally delimiting first auxiliary shielding chamber 31. In particular, lateral plates 50 are transversally, in particular perpendicularly, mounted to main shielding chamber 27, in particular to first principal wall 44.

Preferentially, principal plate 49 comprises access opening 47. Even more preferentially, principal plate 49 also carries a sealing member 51 for sealing access opening 47 for allowing feeding in of web 4 and limiting entrance of gas into first inner space 32 through access opening 47.

In the preferred embodiment shown, first auxiliary shielding chamber 31, in particular first inner space 32, is further delimited by first principal wall 44.

In an alternative embodiment not shown, first auxiliary shielding chamber 31 could comprise a further principal plate parallel to and distanced from principal plate 49 and comprising discharge opening 48. In such an alternative embodiment, outer lateral plates 50 would be also mounted to the further principal plate and the latter would be mounted to first principal wall 44.

In a preferred embodiment, first auxiliary shielding chamber 31 also comprises an extraction opening 52, in particular distinct from the access opening 47, configured to allow to extract gas from first inner space 32 of first auxiliary shielding chamber 31.

In particular, extraction opening 52 is arranged in one of outer lateral plates 50.

In the preferred embodiment shown, sterilization apparatus 9 also comprises a first deviation device, in particular a plurality of rollers 53, arranged within first auxiliary shielding chamber 31 and configured to direct, in use, web 4 along a deviation portion P2 of path P from access opening 47 to inlet opening 29. In particular, in the preferred embodiment, this is necessary as access opening 47 and inlet opening 29 are non-coaxially arranged.

Figure 4:
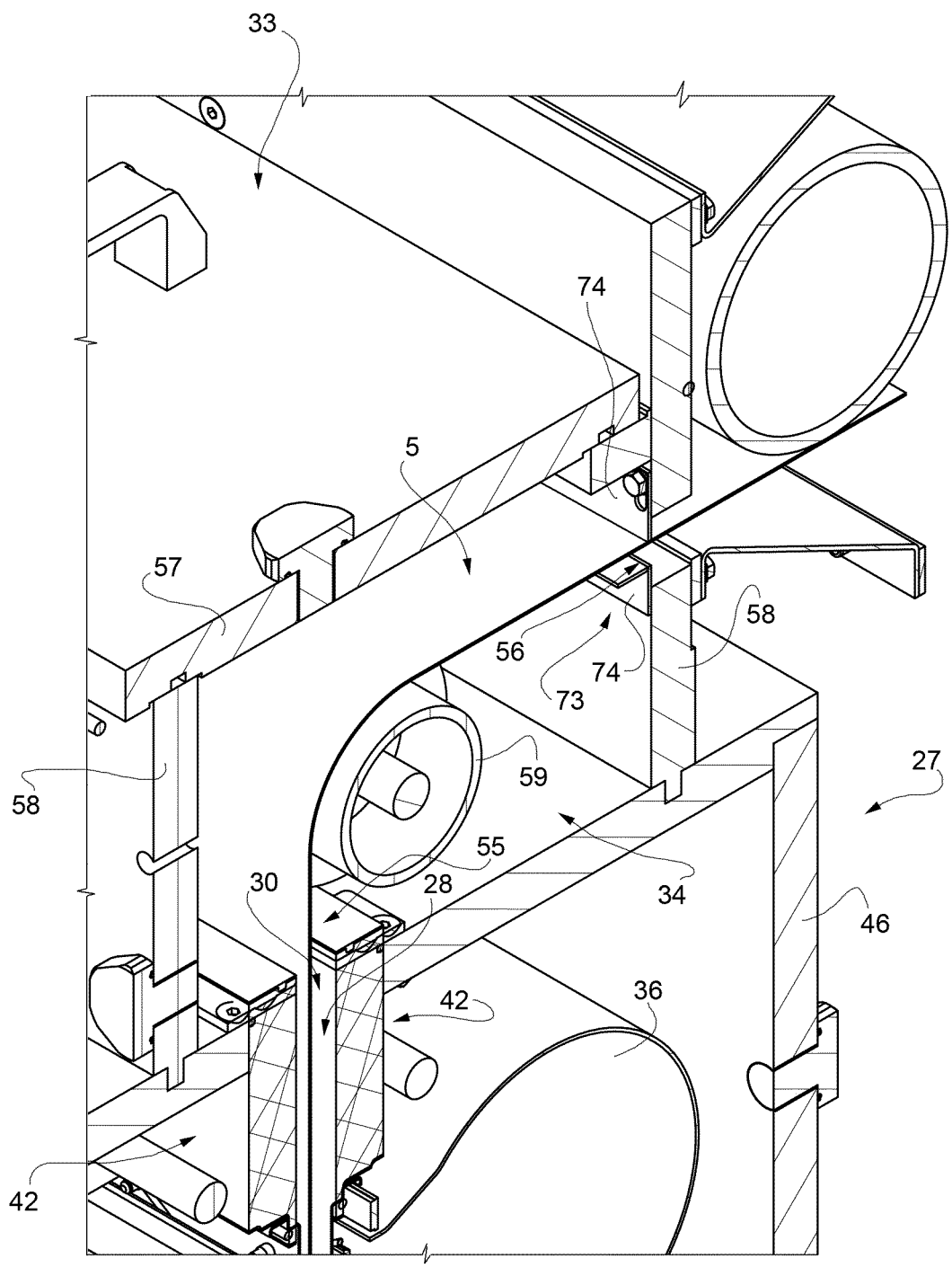
FIG. 4 is a partially sectionized and perspective view of another detail of the sterilization apparatus of FIG. 2.

With particular reference to FIGS. 2 and 4, second auxiliary shielding chamber 33 comprises an access mouth 55 and a discharge mouth 56 for web 4, in particular through which, in use, web 4 respectively enters into and exits from second auxiliary shielding chamber 33.

Preferentially, sterilization apparatus 9 and isolation chamber 14 are connected to one another through second auxiliary shielding chamber 33. In other words, in use, web 4 advances through discharge mouth 56 into isolation chamber 14.

Preferentially, second auxiliary shielding chamber 33 comprises a principal plate 57, in particular distanced from and parallel to first principal wall 44 and second principal wall 45, and outer lateral plates 58 connected to, in particular transversally mounted to, principal plate 57 and laterally delimiting second auxiliary shielding chamber 33. In particular, lateral plates 58 are mounted to main shielding chamber 27, in particular second principal wall 45.

In particular, the lateral plate 58 that delimits isolation chamber 14 comprises discharge mouth 56.

In the preferred embodiment shown, second auxiliary shielding chamber 33 is further delimited by second principal wall 45.

In an alternative embodiment not shown, second auxiliary shielding chamber 33 could comprise a further principal plate parallel to and distanced from principal plate 57 and comprising access mouth 55. In such an alternative embodiment, outer lateral plates 58 would be also mounted to the further principal plate and the latter would be mounted to second principal wall 45.

In the preferred embodiment shown, sterilization apparatus 9 also comprises a second deviation device, in particular at least one roller 59, arranged within second auxiliary shielding chamber 33 and configured to direct, in use, web 4 along a deviation portion P3 of path P from outlet opening 30 to discharge mouth 56.

In a preferred embodiment, sterilization apparatus 9 comprises an aspiration device configured to generate at least:
- a first flow of gas within advancement channel 28 from outlet opening 30 to inlet opening 29 (i.e. the first flow of gas is opposite to the advancement direction of web 4); and
- a second flow of gas from inlet opening 29 to extraction opening 52 and, in particular, out of first inner space 32.

By providing for the first flow of gas from outlet opening 30 to inlet opening 29 it is guaranteed that web 4, in particular first face 5, even more particular also second face 6, remain sterile after the sterilization as any contaminants are directed away from the sterile web 4, in particular the sterile first face 5, even more particular also the sterile second face 6.

By providing for the second flow of gas from inlet opening 29 to extraction opening 52 contaminants and other undesired components such as ozone are removed from sterilization apparatus 9, in particular first inner space 32, in a controlled manner.

Preferentially, the aspiration device is also configured to generate a third flow of gas from second inner space 34 to advancement channel 28, in particular from discharge mouth 56 to outlet opening 30.

Preferably, the aspiration device is also configured to generate a fourth flow of gas from inner environment 15, in particular through discharge mouth 56, into second inner space 34.

In a preferred embodiment, the aspiration device comprises a suction conduct 61 arranged within first inner space 32 and being configured to at least partially guide the second flow of gas, in particular at least to extraction opening 52. Suction conduct 61 has an intake mouth 62 (through which, in use, the gas of the second flow of gas enters) and being arranged in the proximity of inlet opening 29.

In more detail, suction conduct 61 comprises a first conduct portion 63 extending parallel to inlet opening 29 and comprising intake mouth 62 and a second conduct portion 64 being fluidically and, in particular also mechanically, connected to first conduct portion 63 and extraction opening 52.

Preferentially, first conduct portion 63 also comprises a web passage 65 being arranged opposite to intake mouth 62 and being configured to allow, in use, entrance of web 4 into first conduct portion 63. In particular, intake mouth 62 is also configured to allow for the exit of web 4 from first conduct portion 63. In other words, in use, web passage 65 is positioned upstream of intake mouth 62, which again is positioned upstream of inlet opening 39 along path P.

In even further detail, first conduct portion 63 comprises a first structured sheet 66 and a second structured sheet 67 defining in collaboration intake mouth 62 and, in particular also web passage 65. Preferentially, first structured sheet 66 is connected to, in particular fixed to, second conduct portion 64, and second structured sheet 67 is connected to and protrudes from first principal wall 44 into first inner space 32.

Preferentially, the aspiration device also comprises at least one suction device configured to generate the suction force and being fluidically connected to second inner space 34 through a(n) (outer) tubing 68 (only partially shown) connected to first auxiliary shielding chamber 31 in the area of extraction opening 52. Even more preferentially, the aspiration device is configured to direct the gas extracted from first auxiliary shielding chamber 31, in particular first inner space 32, to a regeneration circuit of packaging machine 1.

In a most preferred embodiment, packaging machine 1 comprises pressure control means configured to maintain a first pressure within first auxiliary shielding chamber 31, a second pressure within second auxiliary shielding chamber 33 and a third pressure within isolation chamber 14.

Preferentially, pressure control means are configured to control the first pressure, the second pressure and the third pressure such that the second pressure is higher than the first pressure and the third pressure is higher than the second pressure. In other words, pressure control means are configured to control the first pressure, the second pressure and the third pressure such that the first pressure is lower than the second pressure and the second pressure is lower than the third pressure.

These pressure distributions allow to further guarantee to avoid contaminating the sterile environments within packaging machine 1.

Preferentially, pressure control means are configured to control:
- the first pressure to be substantially constant, in particular to be substantially identical to the atmospheric pressure;
- the second pressure to range between 10 to 60 Pa above ambient pressure, in particular between 20 to 40 Pa above ambient pressure; and
- the third pressure to range between 100 to 600 Pa above ambient pressure, in particular between 200 to 400 Pa above ambient pressure.

In a preferred embodiment, pressure control means comprise a portion of sterilization apparatus 9, in particular a valve 72 coupled to first auxiliary shielding chamber 31 and configured to selectively open or close so as to respectively allow or prevent a gas to enter into first auxiliary shielding chamber 31, in particular first inner space 32, for controlling the first pressure.

Preferentially, pressure control means comprise the aspiration device.

Pressure control means also comprise a sterile gas circuit, in particular a closed sterile gas circuit, configured to introduce sterile gas, in particular sterile air, into isolation chamber 14.

With particular reference to FIG. 4, pressure control means also comprises a restriction group 73 configured to control the pressure drop from isolation chamber 14 to second auxiliary shielding chamber 33.

Preferentially, restriction group 73 comprises two restriction sheets 74 configured to restrict the cross-sectional size of discharge mouth 56.

Even more preferentially, restriction sheets 74 are moveable for allowing to adjust the pressure drop.

In the specific example shown, restriction sheets 74 are manually moveable so as to adjust the relative positions. In an alternative embodiment not shown, pressure control means could comprise an actuator configured to adjust the relative positions of restriction sheets 74.

In use, packaging machine 1 forms packages 2 filled with the pourable product.

In more detail, a method of forming packages 2 comprises the following main steps:
advancing web 4 along advancement path P;
sterilizing at least first face 5 of web 4 at sterilization station 10;
forming tube 3 at tube forming station 18;
longitudinally sealing tube 3;
filling tube 3 with the pourable product;
advancing tube 3 along path Q; and
obtaining single packages 2 from tube 3 by forming tube 3, transversally sealing tube 3 between successive packages 2 and transversally cutting tube 3 between successive packages 2 for obtaining single packages 2.

Preferentially, the method of forming packages 2 also comprises a step of controlling the pressure during which the pressure within at least sterilization apparatus 9 and isolation chamber 14 is controlled.

In more detail, during the main step of advancing web 4, conveying means 22 advance web 4 from magazine unit 7 along advancement path P through sterilization apparatus 9 and to tube forming device 17.

In other words, conveying means 22 advance web 4 from host station 8 to tube forming station 18 through sterilization station 10.

More specifically, the main step of advancing web 4 comprises:
a first sub-step of advancing, during which web 4 advances along deviation portion P2;
a second sub-step of advancing, during which web 4 advances along sterilization portion P1; and
preferentially, a third sub-step of advancing, during which web 4 advances along deviation portion P3.

Even more specifically, during the first sub-step of advancing, web 4 advances through first inner space 32 from access opening 47 to inlet opening 29.

Preferentially, during the second sub-step of advancing, web 4 advances through advancement channel 28 from inlet opening 29 to outlet opening 30.

Preferentially, during the third sub-step of advancing, web 4 advances through second inner space 34 from access mouth 55 to discharge mouth 56.

During the main step of forming tube 3, tube forming device 17 gradually overlaps the opposite lateral edges of web 4 with one another so as to form a longitudinal seam portion.

During the main step of longitudinally sealing tube 3, sealing device 19 seals the longitudinal seam portion.

During the main step of advancing tube 3, conveying means 22 advance tube 3 (and any intermediates of tube 3) along path Q to package forming unit 21.

During the main step of filling tube 3, filling means 20 fill the pourable product into the longitudinally sealed tube 3.

During the main step of obtaining single packages 2, package forming unit 21 forms and transversally seals tube 3 between successive packages 2 and, preferentially, also transversally cuts tube 3 between successive packages 2.

In more detail, during the main step of sterilizing web 4, at least a step of directing a sterilizing irradiation, in particular electromagnetic irradiation, even more particular electron beam irradiation, at least onto first face 5, preferentially also onto second face 6 is executed.

Preferentially, during the main step of sterilizing web 4, the first sub-step of advancing and the second sub-step of advancing, even more preferentially also the third sub-step of advancing, are executed.

Preferentially, during the step of directing a sterilization irradiation, irradiation device 26 directs the sterilizing irradiation, in particular the electromagnetic irradiation, even more particular the electron beam irradiation, at least onto first face 5, preferentially also onto second face 6 for sterilizing first face 5 and, preferentially also second face 6.

In even more detail, during the step of directing a sterilization irradiation, first electron beam emitter 35 directs the electron beam irradiation onto first face 5, and preferentially second electron beam emitter 36 directs the electron beam irradiation onto second face 6 while web 4 is advanced through advancement channel 28 along sterilization portion P1.

Preferentially, the step of directing a sterilization irradiation is executed during the second sub-step of advancing.

Advantageously, during the step of sterilizing also the step of generating a first flow of gas within advancement channel 28 from outlet opening 30 to inlet opening 29 and a second flow of gas from inlet opening 29 to extraction opening 52 are generated and, in particular gas is extracted from first inner space 32.

In more detail, during the step of generating, the second flow of gas flows at least partially through suction conduct 61. Preferentially, the second flow of gas enters suction conduct 61 through intake mouth 62 and flows to extraction opening 52. Even more preferentially, after entering the suction conduct 61, the second flow of gas flows through first conduct portion 63 and then through second conduct portion 64. Then, the second flow of gas is removed from first inner space 32 through extraction opening 52.

In even further detail, during the step of generating, the suction device generates the suction force for generating the first flow of gas and the second flow of gas. Preferentially, the gas is extracted from first inner space 32 through extraction opening 52 and into tubing 68. Even more preferentially, the gas extracted from first inner space 32 is directed into the regeneration circuit.

In more detail, during the step of controlling the pressure, the pressure control means control the first pressure, the second pressure and the third pressure such that the first pressure is lower than the second pressure and the second pressure is lower than the third pressure.

Preferentially, the pressure control means control the pressures such that:
- the first pressure is substantially constant, in particular substantially identical to the atmospheric pressure;
- the second pressure ranges between 10 to 60 Pa above ambient pressure, in particular between 20 to 40 Pa above ambient pressure; and
- the third pressure ranges between 100 to 600 Pa above ambient pressure, in particular between 200 to 400 Pa above ambient pressure.

More specifically, the first pressure is controlled through valve 72. Valve 72 opens to guide a gas into first auxiliary chamber 31 if the first pressure falls below a predetermined pressure value, in particular below atmospheric pressure. The latter case may occur in these cases in which the suction force applied by the suction device would extract gas from first inner space 32 in an amount being larger than the gas entering into first inner space 32 through inlet opening 29.

Preferentially, pressure control means control the third pressure through the sterile gas circuit introducing sterile gas into isolation chamber 14.

Preferentially, the pressure drop between isolation chamber 14 and second auxiliary shielding chamber 33 is controlled by restriction group 73 and the first flow of gas within advancement channel 28 generating a third flow of gas from second inner space 34 towards advancement channel 28, in particular from discharge mouth 56 to outlet opening 30.

The advantages of sterilization apparatus 9 according to the present invention will be clear from the foregoing description.

In particular, sterilization apparatus 9 comes along with a simplified structure with respect to the ones known in the art.

Even more particular, sterilization apparatus 9 allows to remove contaminations and other undesired compositions such as ozone from the sterilization apparatus 9 without the need of an additional isolation housing.

Clearly, changes may be made to sterilization apparatus 9 as described herein without, however, departing from the scope of protection as defined in the accompanying claims.

The invention claimed is:

1. A sterilization apparatus for sterilizing a web of packaging material advancing along a web advancement path, the sterilization apparatus comprising:
- an irradiation device configured to sterilize at least a first face of the advancing web of packaging material by directing a sterilizing irradiation onto at least the first face while, in use, advancing along a sterilization portion of the web advancement path;
- a main shielding chamber housing the irradiation device and comprising an advancement channel having an inlet opening and an outlet opening and through which, in use, the web of packaging material advances along the sterilization portion;
- an auxiliary shielding chamber being arranged upstream of the advancement channel along the web advancement path and having an inner space being in fluid connection with the advancement channel;
- the auxiliary shielding chamber comprising an extraction opening configured to allow to extract gas from the auxiliary shielding chamber;
- an aspiration device configured to generate a first flow of gas within the advancement channel from the outlet opening to the inlet opening and a second flow of gas from the inlet opening to the extraction opening; and the aspiration device comprising a suction conduct arranged within the inner space and configured to at least partially guide the second flow of gas, the suction conduct having an intake mouth arranged at the inlet opening,
wherein the irradiation device is disposed inside the main shielding chamber and outside the auxiliary shielding chamber.

2. The sterilization apparatus according to claim 1, wherein the suction conduct comprises a first conduct portion extending parallel to the inlet opening and comprising the intake mouth and a second conduct portion fluidically connected to the first conduct portion and the extraction opening.

3. The sterilization apparatus according to claim 1, and further comprising a valve configured to selectively open or close so as to respectively allow or prevent a gas to enter into the inner space for controlling the pressure inside the auxiliary shielding chamber.

4. The sterilization apparatus according to claim 1, wherein an access opening of the auxiliary shielding chamber through which the web of packaging material enters into the auxiliary shielding chamber and the inlet opening are non-coaxially arranged with respect to one another.

5. The sterilization apparatus according to claim 4, wherein the sterilization apparatus further comprises a deviation device arranged within the auxiliary shielding chamber and configured to direct, in use, the web of packaging material from the access opening to the inlet opening.

6. The sterilization apparatus according to claim 1, wherein the main shielding chamber comprises two inner walls parallel to one another and distanced from one another so that a space between the inner walls defines the advancement channel.

7. A packaging machine for producing sealed packages of a pourable product from a web of packaging material, the packaging machine comprising:
- an isolation chamber separating an inner environment from an outer environment;
- a tube forming device at least partially arranged within the isolation chamber at a tube forming station and adapted to form a tube from the web of packaging material;
- a sealing device at least partially arranged within the isolation chamber and adapted to longitudinally seal the tube formed by the tube forming device;
- filling means for filling the tube with the pourable product;
- a package forming unit adapted to form and to transversally seal the tube for forming the packages;
- conveying means for advancing the web of packaging material along the web advancement path from a host station to the tube forming station and for advancing the tube along a tube advancement path to the package forming unit; and
- a sterilization apparatus according to claim 1 for sterilizing at least a first face of the web of packaging material at a sterilization station arranged upstream of the tube forming station along the web advancement path.

8. The packaging machine according to claim 7, wherein the sterilization apparatus further comprises a further auxiliary shielding chamber arranged downstream of the advancement channel along the web advancement path and having a further inner space being in fluid connection with the advancement channel; and
wherein the packaging machine further comprises pressure control means configured to maintain a first pressure within the auxiliary shielding chamber, a second pressure within the further auxiliary shielding chamber and a third pressure within the isolation chamber;

wherein the pressure control means are configured to control the first pressure, the second pressure and the third pressure such that the second pressure is higher than the first pressure and the third pressure is higher than the second pressure.

9. Method of sterilizing a web of packaging material comprising:

advancing the web of packaging material along a web advancement path; and directing a sterilizing irradiation onto at least a first face of the web of packaging material;

the advancing of the web comprising a first sub-step of advancing, during which the web of packaging material advances within an inner space of an auxiliary shielding chamber;

a second sub-step of advancing, during which the web of packaging material advances from an inlet opening to an outlet opening of an advancement channel arranged within a main shielding chamber;

the auxiliary shielding chamber is arranged upstream of the advancement channel and the advancement channel and the inner space are in fluid connection with one another, and the irradiation device is disposed inside the main shielding chamber and outside the auxiliary shielding chamber;

the directing of the sterilizing irradiation being executed during the second sub-step of advancing;

generating a first flow of gas within the advancement channel from the outlet opening to the inlet opening and a second flow of gas from the inlet opening to an extraction opening of the auxiliary shielding chamber for extracting gas from the auxiliary shielding chamber; and during the generating of the second flow of gas, the second flow of gas flows at least partially through a suction conduct arranged within the first auxiliary shielding chamber and the second flow of gas enters the suction conduct through an intake mouth of the suction conduct, the intake mouth being arranged at the inlet opening.

10. The method according to claim 9, wherein during the generating of the second flow of gas, the second flow of gas flows within a first conduct portion of the suction conduct extending parallel to the inlet opening and comprising the intake mouth and through a second conduct portion fluidically connected to the first conduct portion and the extraction opening.

11. The method according to claim 9, and further comprising controlling the pressure during which the pressure within the auxiliary shielding chamber is maintained at a predetermined pressure value.

12. The method according to claim 11, wherein during the controlling of the pressure a valve is selectively controlled to allow or prevent selective introduction of gas into the auxiliary shielding chamber.

* * * * *